United States Patent
Samuelsson et al.

[19]

[11] Patent Number: 6,100,442
[45] Date of Patent: Aug. 8, 2000

[54] ABSORBENT ARTICLE WITH IMPROVED LEAKAGE SECURITY

[75] Inventors: Ann Samuelsson, Lindome; Charlotte Persson, Göteborg; Solgun Drevik, Mölnlycke, all of Sweden

[73] Assignee: SCA Hygiene Products Aktiebolag, Gothenburg, Sweden

[21] Appl. No.: 09/100,123

[22] Filed: Jun. 19, 1998

[30] Foreign Application Priority Data

Jun. 24, 1997 [SE] Sweden ................................ 9702396

[51] Int. Cl.[7] ............................................. A61F 13/15
[52] U.S. Cl. ..................................... 604/378; 604/385.1
[58] Field of Search ................................ 604/378, 385.1, 604/385.2, 386, 387, 389

[56] References Cited

U.S. PATENT DOCUMENTS

| H1634 | 2/1997 | Oetjen et al. . | |
| Re. 24,137 | 4/1956 | Jacks | 604/378 |
| 3,115,877 | 12/1963 | Harwood | 604/385.1 |
| 3,528,422 | 9/1970 | Hodas | 604/385.1 |
| 4,490,147 | 12/1984 | Pierce et al. . | |
| 4,627,848 | 12/1986 | Lassen et al. | 604/370 |
| 5,188,624 | 2/1993 | Young, Sr. et al. | 604/385.1 |
| 5,545,156 | 8/1996 | DiPalma et al. . | |
| 5,672,165 | 9/1997 | Belecky et al. | 604/383 |
| 5,873,869 | 2/1999 | Hammons et al. | 604/385.1 |

FOREIGN PATENT DOCUMENTS

| 2 653 328 | 4/1991 | France . |
| 507 798 | 7/1998 | Sweden . |
| WO 94/10956 | 5/1994 | WIPO . |
| WO94/10953 | 5/1994 | WIPO . |
| WO94/22060 | 5/1994 | WIPO . |

*Primary Examiner*—John G. Weiss
*Assistant Examiner*—Dennis Ruhl
*Attorney, Agent, or Firm*—Burns, Doane, Swecker & Mathis, L.L.P.

[57] ABSTRACT

An absorbent article such as a sanitary napkin, a panty liner or an incontinence pad, which is intended to be substantially accommodated within a user's panties and comprising an upper absorbent part (2) and a lower absorbent part (3), whereby the upper absorbent part (2) forms a raised portion (26) projecting from the lower absorbent part (3) and has a lesser extension in the transverse direction of the article than the lower absorbent part (3). A porous liquid acquisition layer (28) is arranged between the two absorbent parts (2,3) and has a density which is less than the density in both the upper absorbent part (2) and the lower absorbent part (3).

17 Claims, 2 Drawing Sheets

ABSORBENT ARTICLE WITH IMPROVED LEAKAGE SECURITY

TECHNICAL FIELD

The present invention relates to an absorbent article such as a sanitary napkin, a panty liner or an incontinence pad, which article is intended to be substantially accommodated within the panties of a user and comprising a first absorbent part and a second absorbent part, which two parts are mutually joined.

BACKGROUND OF THE INVENTION

A basic requirement for an absorbent article such as a sanitary napkin or the like is that the article must be shaped in such a manner that it can collect and absorb all discharged bodily fluid.

Since, for example, sanitary napkins are intended to be accommodated within a pair of normal panties, they are relatively small and, above all, often rather narrow. There is therefore an obvious risk that, by misplacing such an article within the panties or by it being deformed during use, it will not present a sufficiently large receiving surface for the discharged bodily fluid.

For example, it is not uncommon for the absorbent article to be placed too far forward or too far backwards or offset somewhat transversely. Another commonly occurring reason for bodily fluid to leak past an absorbent article and to soil the user's clothing is that the article is compressed between the legs of the user and thus becomes so narrow that the surface available for absorption becomes insufficient. Neither is it unusual for the side edges of the article to become folded over the surface of the article and thereby reduce the available surface.

An absorbent article of the type under consideration is generally maintained in the panties of the user by means of self-adhesive glue and/or a friction coating. When placing the article in the panties, it is difficult to obtain a placement which is optimal in relation to the body of the user. Normally, the crotch portion of the panties is used to determine where the article is to be placed. However, since panties are manufactured in a surprisingly large number of different models and sizes, the position and shape of the central portion provides an extremely unreliable indication of where in the panties an absorbent article should be positioned.

One way to reduce the risk of edge leakage due to deformation of the article during use is to provide the article with a preformed raised portion which, during use, is intended to contact the user's genitalia. In this manner, discharged bodily fluid can be intercepted as soon as it exits the user's body and be immediately absorbed within the article instead of running over its surface. In addition, a raised portion facilitates the placement of the absorbent article by the user in a correct position in relation to her body.

For this purpose, a raised portion of the type which is described in Swedish Patent Application No. 9604221-3 is particularly suitable. Such a raised portion has a predictable shape both before and during use and it maintains its shape irrespective of the movements of the user and the wetting to which the article is subjected. The raised portion is anatomically shaped, which implies that it is relatively narrow so as to be able to be inserted somewhat between the labia of the user during use without creating discomfort for the user.

Even though such a raised portion generally functions satisfactorily, it has been shown that, should the raised portion be subjected to large quantities of bodily fluid during a relatively short time, there is a risk that a quantity of the liquid will run over the side edges of the absorbent article. For example, such leakage can arise when the user of a sanitary napkin has been sitting or lying down for a long period and then suddenly gets up. Since the user has been sitting or lying down, a relatively large quantity of menstrual fluid collects in the user's vagina. As a result of a sudden change in body position, the entire quantity of collected fluid can be discharge in one go. A narrow raised portion of the type which is described in SE 9604221-3 does not therefore have a sufficiently large surface to be able to receive and absorb the entire quantity of liquid at once, which is why such sudden liquid flows often result in leakage.

SUMMARY OF THE INVENTION

In accordance with the present invention, however, an improved absorbent article of the above-mentioned type is provided which is considerably less prone to the risk of leakage.

An article in accordance with the invention is primarily characterized in that a proud liquid acquisition layer is arranged between an upper absorbent part and a lower part, whereby the liquid acquisition layer has a density which is less than the density in the upper absorbent part.

Advantageously, the liquid acquisition layer is compressible, whereby the upper part has the possibility during absorption to swell and displace the material in the liquid acquisition layer. In this manner, the absorption capacity in the upper part can be utilized optimally without the shape of the upper part against the user's body being significantly changed. An absorbent article of this type thus remains a good fit during use even after absorption of bodily fluid.

It is also preferable, though not necessary, that the lower part also be absorbent. In such a case, the liquid acquisition layer's density is less than the density in both the upper absorbent part and the lower absorbent part.

By arranging a porous liquid acquisition layer between the two constituent parts of the article, it is possible during a second absorption stage to collect any bodily fluid which flows over the outside of the upper part. This prevents the bodily fluid from flowing out past the edges of the article which would result in leakage. Instead, the bodily fluid can flow in under the upper part and be absorbed by the absorption material in the upper part and, where appropriate, in the lower part. It is therefore suitable that the lower part of the absorbent article is cupped or curved in the transverse direction of the article so that the liquid runs under the influence of gravity into the pores of the liquid acquisition layer and in towards the longitudinal central line of the article, i.e. in under the upper part.

In order to provide the absorbent article with an anatomically correct shape, the upper absorbent part has an extension in the transverse direction of the article which is less than the extension of the lower part in the transverse direction. A particularly advantageous size relationship is attained if the upper part's width in the crotch portion is between ¼ and ⅓ of the lower part's width.

In a corresponding manner, the upper absorbent part should have a lesser extension in the longitudinal direction than the lower part and should thus be between ⅓ and ¾ of the length of the lower part.

According to a preferred embodiment, the liquid acquisition layer has an extension in the transverse direction of the article which is greater than the upper absorbent part's extension in the transverse direction, though suitably less than the lower part's extension in the transverse direction.

In this manner, liquid which flows on the upper part is collected in the porous material in the liquid acquisition layer and flows in between the two parts of the article.

In a corresponding manner, the liquid acquisition layer can have an extension in the article's longitudinal direction which is greater than the extension of the upper absorbent part in the longitudinal direction, though less than the extension of the lower part in the longitudinal direction. With such an embodiment, the risk of leakage at the end edges of the article is reduced.

The liquid acquisition layer can consist of numerous different types of porous, preferably compressible, material. A preferred liquid acquisition layer is a fibre wadding. This can be bonded using any of the available methods within this field. For example, the fibre wadding may contain thermoplastic fibres which are melted and thus bond the fibre wadding together. Other ways of bonding a fibrous structure are through application of particular binders, such as latex, or thermoplastic adhesive, needling, using high-pressure water jets, ultrasound or the like.

The fibre wadding can comprise highly resilient fibres both in the wet and dry condition. An example of a fibre material which has been shown to function well is a material layer consisting of a mixture of 70% polypropylene fibres treated with a wetting agent and 30% rayon fibres.

Alternatively, or in combination with a resilient fibre wadding, it is possible that the liquid acquisition layer comprises a layer of a bonded material substantially consisting of air-laid cellulose fibres.

A further material which can be used as the liquid acquisition layer is porous foam material.

In order to be able to receive liquid, at least the surface of the upper absorbent part which faces the user during use must be liquid-permeable. This can be achieved, for example, by encasing the absorbent material in the upper part in a liquid-permeable casing. Suitable casing materials are thus nonwoven material, perforated plastic films, nets, loose fabric, or the like. The casing can either be arranged over only the upper absorbent part or it can encase the entire absorbent article. In the latter case, the casing suitably comprises a liquid-impermeable component placed over the surface of the article which, during use, is intended to face away from the user. In addition, the lower part of the article can also be provided with a liquid-permeable casing layer. Such a casing layer can thus be the same as, or of a different type to, the casing layer of the upper part. According to one embodiment, the portions of the liquid-permeable casing layer which are intended to come into contact with the user's mucous membranes during use is made from a hydrophillic absorbent material, whilst casing portions intended to come into contact with skin are preferably non-absorbent. Thus, it can be suitable that the upper part's casing consists of a smooth material with no projecting binding pattern and having certain absorption capacity. In this manner, a certain quantity of moisture will remain in the casing. This serves to reduce the risk of the mucous membranes drying out and becoming irritated. The liquid-permeable outer layer on the lower part will be substantially in contact with the user's skin during use. This outer layer should therefore be soft and airy and substantially non-absorbent. In this manner, an outer layer is attained which keeps the skin dry and which does not mechanically chafe, or in any other way irritate, the skin. One method of attaining a soft and airy outer layer is by using a nonwoven material with a relatively sparse binding pattern. Other materials which may be used which provide a dry surface are perforated plastic films and plastic nettings.

BRIEF DESCRIPTION OF THE DRAWINGS

The invention will be described in greater detail in the following with reference to embodiments shown in the attached drawings. Thus.

DETAILED DESCRIPTION OF PREFERRED EMBODIMENTS

Figure 1:
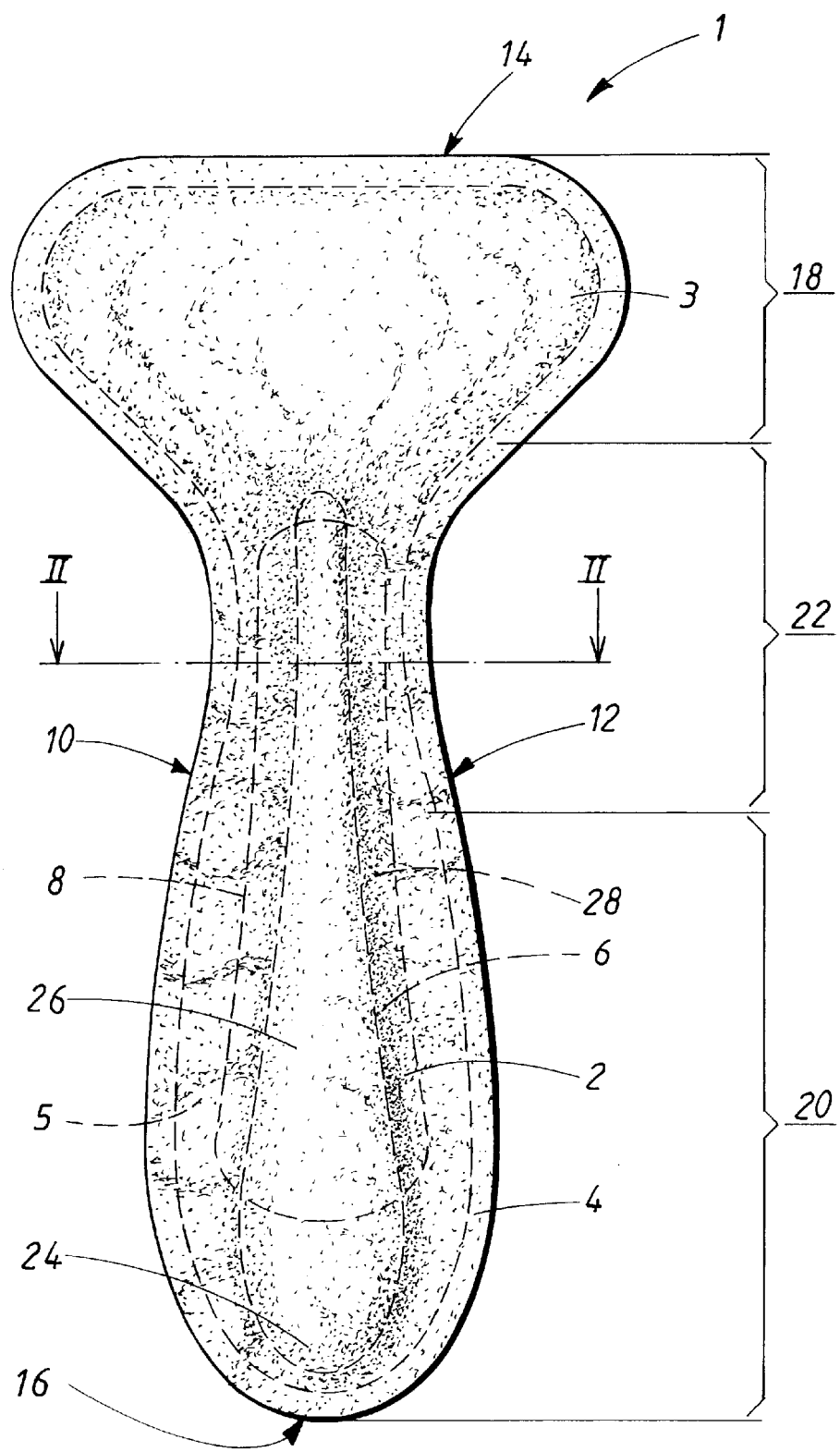
FIG. 1 shows a sanitary napkin viewed from the side which during use is intended to face the user.
Figure 2:
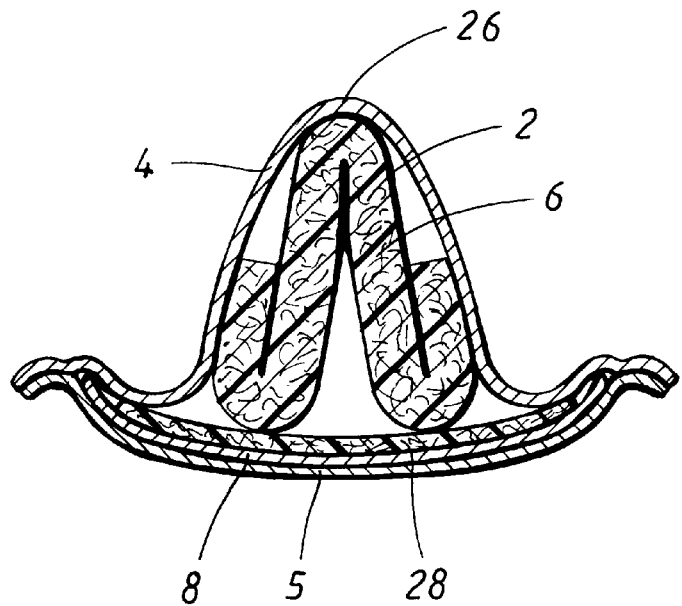
FIG. 2 is a sectional view along line II—II through the sanitary napkin of FIG. 1.

The sanitary napkin 1 shown in FIGS. 1 and 2 is made of an upper absorbent part 2 and a lower absorbent part 3. When the sanitary napkin is being used, the upper absorbent part 2 is intended to contact the user's body and collect and absorb the majority of the bodily fluid which is discharged onto the sanitary napkin. The two parts are encased in a casing consisting of a liquid-permeable topsheet 4 and a liquid-impermeable back sheet 5, which sheets are mutually joined around the absorbent parts 2,3, for example by gluing or welding.

Alternatively, the upper absorbent part 2 can be provided with a separate liquid-permeable topsheet which extends underneath the upper part. With such an embodiment, it is suitable if a further liquid-permeable casing layer is arranged over the lower part and connected to the liquid-impermeable back sheet 5.

The upper absorbent part comprises an absorbent body 6 which is dimensioned to be able to receive and absorb the majority of the bodily fluid which is discharged onto the sanitary napkin during use.

The liquid-permeable topsheet 4 is suitably made from a soft, skin-friendly and flexible material of the type which is normally used as surface material in absorbent articles. Examples of such materials are perforated plastic films, nonwoven fabrics (normally termed nonwoven material), nets of fabric or plastic made by stitching, crocheting, braiding, moulding or the like, as well as conventional woven fabric material, of course.

The absorbent body 6 may also be of any type suitable for the stated purpose. Thus, the absorbent body 6 can be made from one or more layers of absorbent fibres such as cellulose fluff pulp, rayon, cotton or the like, and tissue material, nonwoven material, foam or other absorbent or non-absorbent components.

In order to increase the absorbent capacity, the absorbent body 6 can comprise so-called superabsorbents which are polymer materials, normally present in the form of particles, flakes, fibres or the like and having the ability to absorb several times their own weight of bodily fluid during formation of an aqueous gel. Superabsorbents can be present in one or more layers or regions in the absorbent body 6, or can be mixed with other absorbent materials such as cellulose fluff pulp or absorbent fibre waddings of another type. Of course, the superabsorbents can also be present in a non-absorbing support structure, for example a fibre layer of non-absorbing fibres.

In order to achieve good shape stability in the upper part 2 of the sanitary napkin, it is suitable if at least some component in the upper part 2 is stiff and rigid so that the upper part maintains its shape during use. Sufficient stiffness can be attained by heavily compressing the absorbent material, by using a particular shape-stabilizing and stiffness-increasing insert, or by selecting an absorbent material with high shape-retention and stiffness. Of course, it is possible to combine different materials so that the desired stiffness is attained.

One type of absorbent material which has been shown to be particularly suitable for the purpose is described in WO 94/10953 and WO 94/10956. These materials are present in the form of dry-defibrated fibre layers of high density and stiffness. The fibre layers are used directly in an absorbent article without being firstly defibrated. The fibre layers have high stiffness and the ability to resist pressure deformation, whereby an absorbent body 6 comprising such material offers good shape stability. In addition, the fibre materials have very high absorption capacity and capillary action, which implies that the absorbent body 6 in the upper part 2 can be made small and narrow, yet still meet the requirements of being able to absorb the majority of the bodily fluid discharged onto the sanitary napkin.

The upper absorbent part 2 is shaped so as to be able to contact the user's genitalia and, as already mentioned, should have sufficient absorption capacity for the majority of the discharged bodily fluid to be able to be absorbed by the absorbent body 6.

As with the upper absorbent part 2, the sanitary napkin's lower absorbent part 3 comprises an absorbent body 8 arranged immediately within the liquid-impermeable back sheet 5. The liquid-permeable back sheet 5 is thus intended during use to face away from the user.

The liquid-impermeable back sheet 5 consists of a liquid-impermeable, shape-stable shell of a stiff material, preferably plastic. The material in the back sheet 5 can thus be so stiff that the back sheet 5 substantially resists compression and deformation in the transverse direction of the sanitary napkin during use.

The sanitary napkin 1 shown in FIGS. 1 and 2 has a substantially elongate shape with two longitudinally extending side edges 10,12 and two transverse end edges 14,16. Furthermore, the sanitary napkin presents a relatively wide, bowl-shaped forward portion 18, a rounded raised rearward portion 20 and an intermediate crotch portion 22.

In the sanitary napkin's crotch portion 22, the liquid-impermeable back sheet 5 is relatively narrow in relation to its length and has a width which suitably lies between 1 and 4 cm and preferably about 3 cm. Measurements have shown that there is a space-restricting, critical region in the groin region between two muscle groups which extend from inside the pelvic floor and down each thigh. The distance between the two muscle groups in the genital area has been found to be surprisingly similar in all people, irrespective of body shape and condition. The distance between a user's thighs is thus of course affected by fatty tissue, whilst the distance between the muscle groups in the user's groin is substantially constant, irrespective of whether the user is slim, of normal weight or overweight.

During measurements, it has been shown that that which determines whether a user suffers discomfort in the form of pressure or chafing against the inside of the thighs is whether the absorbent article has a width during use which, in the critical region, noticeably exceeds the distance between the muscle groups in the groin region. This distance has been found to be between about 30 and 35 mm. In addition, it has been shown that an article with a width during use which exceeds 40 mm in the critical region is regarded by the majority of users as being uncomfortable to wear. On the other hand, an absorbent article which presses against or projects beneath the fatty tissues which can be present in the groin region is rarely regarded as uncomfortable.

In conventional absorbent articles, the restricted space in the user's groin implies that the articles are compressed in an uncontrolled manner between the user's legs and become creased so as to be able to be accommodated in the groin. If, however, some component of the absorbent article has such stiffness that it cannot easily be compressed by the forces which normally arise during use, compression can of course only take place to a limited amount. It is therefore primarily for reasons of comfort that the width of the absorbent article in the crotch region does not exceed the critical value which can be tolerated by the user. A certain ability to be compressed in a controlled manner can be achieved by providing the article with deformable zones. Such deformable zones, can, for example, be in the form of soft edges, longitudinally extending material folds or material weakenings such as holes, thinner material portions or the like.

It is of course true that it is the width the article has during use which is relevant for the determination of whether or not there is a risk of chafing. Soft components which are deformed during use do not therefore contribute to the same extent to the width of the article during use as relatively non-compliant components would do.

If the material which is used as the liquid-impermeable back sheet 5 is so stiff that it cannot be deformed in the transverse direction by the compressive forces which arise between the user's thighs, the width of the liquid-impermeable layer must not exceed about 40 mm and preferably not exceed about 35 mm, at least within the part which, during use, is intended to be placed in the critical region between the users legs. Plastic films which have been shown to be suitable for use in such stiff liquid-impermeable back sheets 5 are, for example, layers of polyethylene plastic, filled polypropylene plastic or polyester having a thickness of between about 0.5 and 1 mm.

It does, however, lie within the scope of the invention to use conventional, flexible liquid-impermeable casing materials instead, such as thin plastic films, liquid-impermeable nonwoven material, foam material or the like.

With the sanitary napkin 1 shown in FIGS. 1 and 2, the shape of the napkin can be maintained by making the entire liquid-impermeable back sheet 5 of a substantially shape-stable shell for the remaining components of the sanitary napkin. The sanitary napkin 1 is curved in both the longitudinal and transverse direction to provide the sanitary napkin with a correct anatomical form. Thus, the forward portion 18 is angled forwardly in the direction towards an imaginary user and curved in the transverse direction. In this manner, a softly rounded bowl is attained which fits to the shape of the user's pubic mons. In a corresponding manner, the back sheet 5 is shaped with a raised portion 24 in the rearward portion 20 of the sanitary napkin. The raised portion 24 in the rearward portion 20 is thus intended to pass into the space behind the user's vestibule and to be accommodated in the forward portion of the creases between the user's buttocks. Due to the anatomically adapted shape of the sanitary napkin, it can be maintained during use between the user's legs in contact with the user's body without the need for any particular attachment means.

The upper absorbent part 2 of the sanitary napkin is elongate and relatively narrow. In order to fit to the user's anatomy in the relevant region, the upper part 2 is shaped so that it is narrowest and lowest at the sanitary napkin's forward portion 18 and increases in width and thickness, or height, in a direction towards the rearward portion 20. In this manner, the upper part 2 creates a peak-like raised portion 26 adapted to the shape of the body on the side of the sanitary napkin which, during use, is intended to face the user.

A suitable construction of the upper part 2 is described in Swedish Patent Application No. 9604221-3 in Swedish Patent Application No. 9604225-4. The former patent application describes a shape-permanent upraised portion on an absorbent article, whilst the latter application describes the use of a shape-stabilizing, stiff insert in the raised portion.

The upper part 2 is both narrower and shorter than the lower part 3. In this manner, the upper part 2 is totally covered by regions of the lower part 3. Furthermore, a porous liquid acquisition layer 28 of preferably compressive material is arranged between the upper part 2 and the lower part 3. The liquid acquisition layer 28 in the shown example is somewhat shorter and wider than the upper part 2. In addition, in the shown example, the liquid acquisition layer 28 is narrower than the lower absorbent part 3, though it lies within the scope of the invention that it can be as wide as the lower part.

Material which has been shown to be suitable for use as a liquid acquisition layer 28 is, for example, resiliently bonded, or non-bonded, wadding layers of low density, porous foam material or the like. The liquid acquisition layer 28 can consist of a material which in itself is totally non-absorbent but which has been treated with a wetting agent so that it has a hydrophillic surface. In such materials, liquid can only be received in the pores of the liquid acquisition layer 28. Alternatively, the material can display certain absorption characteristics or consist totally or partially of a conventional absorbent material such as rayon, cellulose fluff pulp or the like. It has been shown that a liquid acquisition layer which works well should have a density between about 40 kg/m$^3$ and about 70 kg/m$^3$ if the density of the absorption material in the surrounding parts 2,3 is between 100–400 kg/m$^3$.

Two materials having mutually different properties, but which have both been found to work well for the stated purpose, are a wadding layer consisting of a mixture of 30% rayon fibres and 70% polypropylene fibres and an air-laid latex-bound material consisting substantially of cellulose fluff pulp. The former material forms a springy, resilient liquid acquisition layer 28 with only restricted absorbability. Such a liquid acquisition layer substantially maintains its shape even after it has been wetted. The material layer which consists of cellulose fluff pulp functions initially as an entrance path for liquid, but collapses after wetting and thus loses its porous structure. In both cases, the liquid acquisition layer 28 can be compressed by the surrounding absorbent parts 2,3 when these absorb liquid and swell. This implies that the absorption material in the upper part 2 can be permitted to swell somewhat without the raised portion 26 in the upper part 2 increasing noticeably in height. Since just a small increase in the size of the raised portion 26 can cause considerable discomfort to the user, it is of course a considerable advantage that the liquid acquisition layer 28 has the described buffer function.

It is of course possible to make the liquid acquisition layer 28 as a laminate of two or more layers, where at least one layer is resilient and at least one layer collapses during wetting.

At least in its dry condition, and preferably also when it is wet, the liquid acquisition layer 28 has a lesser liquid affinity than the absorption material both in the upper absorbent part 2 and the lower absorbent part 3. This implies that liquid which as run into the liquid acquisition layer 28 will be further absorbed by the upper part 2 or the lower part 3. The difference in liquid affinity can be attained by different degrees of compression of the upper absorbent part 2 and the lower absorbent part 3, or by selecting materials having different hydrophillicity.

By the placement of the liquid acquisition layer 28 beneath the upper part 2, liquid which has not managed to be absorbed by the upper part 2 can flow into the porous liquid acquisition layer and from there be received by the absorption material in the two surrounding absorbent parts 2,3. It is therefore suitable that the lower part 3, at least in the area of the liquid acquisition layer 28, is cupped in the transverse direction so that the side edges 10, 12 are somewhat raised from the portion of the lower part 3 which, during use, is positioned directly beneath the upper part 2. With such a shaping of the lower part 3 liquid transport in the liquid acquisition layer 28 is facilitated so that the liquid which is received in the layer due to the effect of gravity flows into the pores of the liquid acquisition layer 28 and in between the upper absorbent part 2 and the lower absorbent part 3.

In order to attain sufficient capacity to be able to receive liquid which flows on the surface of the upper part 2, the liquid acquisition layer should have a thickness in a dry, unused sanitary napkin which is between about 0.3 mm and about 7 mm. Suitably, the thickness is about 1.5–3 mm.

The absorption material in the absorbent body 8 of the lower part 3 can be of any suitable type. The upper part's and the lower part's absorbent bodies 6,8 can thus be made from the same or different material or material combinations. However, both parts must have a density which is greater than the density in the intermediate liquid acquisition layer 28 so that liquid transport between the liquid acquisition layer 28 and either of the absorbent parts 2,3 preferably takes place in a direction from the liquid acquisition layer 28 to the respective absorbent part 2,3.

The upper part 2 can be permanently attached to the lower part 3 and the liquid acquisition layer 28 by means of, for example, gluing, welding or stitching. Alternatively, the upper part can be removably attached, for example by the use of attachment means in the form of hook and loop surfaces, resealable adhesive lines, hooks, clasps, snap fasteners or the like, which permit repeated releasing and fastening of the upper part to the lower part. In the latter case, only the lower part 3 and the liquid acquisition layer 28 are encased between the liquid-permeable casing layer 4 and the liquid-impermeable back sheet 5. The upper absorbent part 2 should thus be encased in a separate liquid-permeable casing or be made from an absorbent body of sufficient surface integrity not to need a particular casing layer. Since the upper part is removable, it is conceivable that the upper parts be made with different absorption capacities and/or with different shapes and/or sizes. In this manner, it is possible for each user to determine herself which upper part is most suitable for her needs.

It is therefore conceivable that a user initially takes advantage of the possibility to use the sanitary napkin shown in FIGS. 1 and 2 with both the upper part and the lower part 3. Thereafter, the upper part 2 can be removed from the lower part 3 and discarded, whilst the lower part 3 remains in the panties and is used on its own.

A particular case is thus absorbent articles which are used for slightly incontinent fertile women. The user of such an article can choose to use only the lower part 3 with the liquid acquisition layer 28 during the time between periods. Such an article has the capability to quickly receive large quantities of urine since the porous liquid acquisition layer 28 has good liquid take-up capability and serves as a reservoir layer from which liquid can thereafter be further absorbed in the denser absorbent body 8 in the lower part 3. During menstruation, the upper part 2 can be attached to the lower part 3, whereby a combined pad is obtained having the capability to receive and absorb urine and menstruation fluid. Of course, if so desired, the user can use both the upper part 2 and the lower part 3 even between periods. In this case, the upper part 2 serves primarily as an indicator which assists the user in placing the pad in a correct position in relation to her body.

In the shown example, the sanitary napkin lacks particular means for attachment within the user's panties. This is because the particular anatomically shaped embodiment of the sanitary napkin, in combination with the hard, shape-permanent back sheet 5, implies that the sanitary napkin can be maintained in contact with the user's body without such attachment means. In sanitary napkins and incontinence pads of more conventional construction, i.e. with flexible and compressible casing layers and absorbent bodies, it is however suitable to use attachment means. Such attachment means can thus be of any type which is common in this field. Examples of common attachment means are friction coatings, self-adhesive glue, attachment flaps, hook and loop surfaces and girdles.

Figure 3:
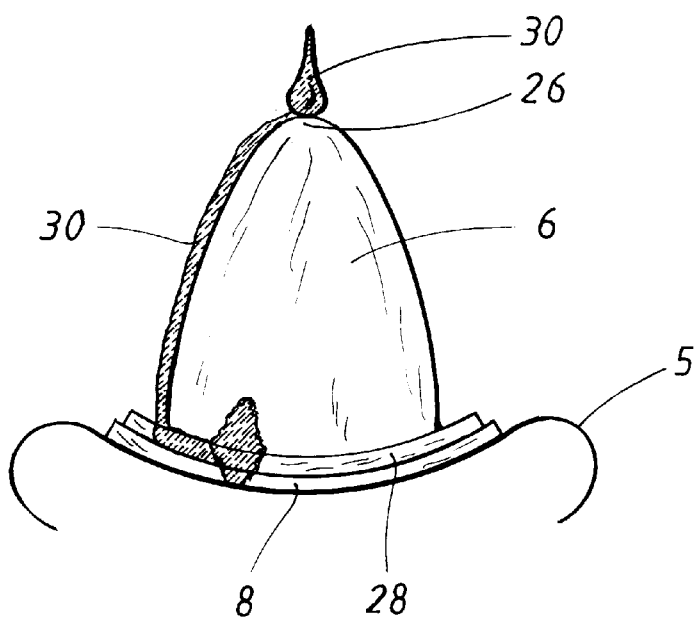
FIG. 3 is a schematic view of the liquid migration in the sanitary napkin of FIGS. 1 and 2.

In FIG. 3 it is schematically shown how liquid 30 which runs over the surface of the sanitary napkin's upper part is absorbed by the sanitary napkin. When the liquid 30 reaches the liquid acquisition layer 28, the liquid runs in underneath the upper part. The open porous structure of the liquid acquisition layer 28 implies that liquid is quickly released into the layer 28. Because the layer has relatively coarse pores, the flow resistance in the layer is low, which means that the liquid 30 manages to flow a distance in under the upper part 2 before it begins to be absorbed by the denser fibre structure in the absorbent bodies 6,8 in the upper and lower parts 2,3 respectively.

In this manner, a more efficient use of the absorption capacity of the two absorbent part 2,3 is attained.

The invention is not to be regarded as being restricted to the embodiments described herein, but instead a number of further variants and modifications are conceivable within the scope of the appended claims. In addition, all possible combinations of the described embodiments are intended to be included in the invention.

What is claimed is:

1. An absorbent article which is intended to be substantially accommodated within a user's panties, which article has a longitudinal direction and a transverse direction and comprises a liquid-permeable layer and a liquid-impermeable layer, and further comprises an upper absorbent part and a lower part, whereby the upper absorbent part is situated at the liquid-permeable layer and the lower part is situated at the liquid-impermeable layer, whereby the upper absorbent part forms a raised portion projecting from the lower part and has a lesser extension in the transverse direction of the article than the lower part, wherein a porous liquid acquisition layer is arranged between the upper absorbent part and the lower part, whereby the liquid acquisition layer has a density which is less than the density of the upper absorbent part, and wherein the lower part is absorbent and in that the density of the liquid acquisition layer is less than the density of both the upper absorbent part and the lower absorbent part.

2. Absorbent article according to claim 1, wherein the liquid acquisition layer is compressible.

3. Absorbent article according to claim 1, wherein the liquid-impermeable surface is in the form of a liquid-impermeable shell.

4. Absorbent article according to claim 1, wherein the density of the liquid acquisition layer is between about 40 kg/m$^3$ and about 70 kg/m$^3$ and the density of an absorption material in the upper part is between 100 and 400 kg/m$^3$.

5. The absorbent article according to claim 1, wherein the absorbent article is a sanitary napkin, a panty liner, or an incontinence pad.

6. Absorbent article according to claim 1, wherein the liquid acquisition layer has an extension in the article's transverse direction which is greater than an extension of the upper absorbent part in the transverse direction.

7. Absorbent article according to claim 6, wherein the extension of the liquid acquisition layer in the article's transverse direction is less than an extension of the lower part in the transverse direction.

8. Absorbent article according to claim 1, wherein the liquid acquisition layer is made from a fibre wadding.

9. Absorbent article according to claim 8, wherein the liquid acquisition layer comprises fibres with resiliency both in a wet and dry condition.

10. Absorbent article according to claim 9, wherein the liquid acquisition layer comprises a material layer consisting of a mixture of 70% polypropylene fibres treated with a wetting agent and 30% rayon fibres.

11. Absorbent article according to claim 8, characterized in that the liquid acquisition layer (28) comprises a layer of a bonded material comprising air-laid cellulose fibres.

12. An absorbent article, which article is intended to be substantially accommodated within a user's panties, which article has a longitudinal direction and a transverse direction and comprises a liquid-permeable layer and a liquid impermeable layer, and further comprises an upper absorbent part and a lower part, whereby the upper absorbent part is situated at the liquid permeable layer and the lower part is situated at the liquid-impermeable layer, whereby the upper absorbent part forms a raised portion projecting from the lower part and has a lesser extension in the transverse direction of the article than the lower part, wherein a porous liquid acquisition layer is arranged between the upper absorbent part and the lower part, whereby the liquid acquisition layer has a density which is less than the density of the upper absorbent part, wherein the liquid acquisition layer has an extension in the article's longitudinal direction which is greater than an extension of the upper absorbent part in the longitudinal direction, though less than an extension of the lower part in the longitudinal direction.

13. The absorbent article according to claim 12, wherein the absorbent article is a sanitary napkin, a panty liner, or an incontinence pad.

14. An absorbent article, which article is intended to be substantially accommodated within a user's panties, which article has a longitudinal direction and a transverse direction and comprises a liquid-permeable layer and a liquid-impermeable layer, and further comprises an upper absorbent part and a lower part, whereby the upper absorbent part is situated at the liquid-permeable layer and the lower part is situated at the liquid-impermeable layer, whereby the upper absorbent part forms a raised portion projecting from the lower part and has a lesser extension in the transverse direction of the article than the lower part, wherein a porous liquid acquisition layer is arranged between the upper absorbent part and the lower part, whereby the liquid acquisition layer has a density which is less than the density of the upper absorbent part, wherein the liquid acquisition layer comprises a layer of porous foam material.

15. The absorbent article according to claim 14, wherein the absorbent article is a sanitary napkin, a panty liner, or an incontinence pad.

16. An absorbent article, which article is intended to be substantially accommodated within a user's panties, which article has a longitudinal direction and a transverse direction and comprises a liquid-permeable layer and a liquid-impermeable layer, and further comprises an upper absorbent part and a lower part, whereby the upper absorbent part is situated at the liquid-permeable layer and the lower part is situated at the liquid-impermeable layer, whereby the upper absorbent part forms a raised portion projecting from the lower part and has a lesser extension in the transverse direction of the article than the lower part, wherein a porous liquid acquisition layer is arranged between the upper absorbent part and the lower part, whereby the liquid acquisition layer has a density which is less than the density of the upper absorbent part, wherein the liquid-impermeable layer is in the form of a liquid-impermeable shell, and the shell is cupped in a direction away from the liquid-permeable layer.

17. The absorbent article according to claim 16, wherein the absorbent article is a sanitary napkin, a panty liner, or an incontinence pad.

* * * * *